(12) United States Patent
Wienecke

(10) Patent No.: US 7,242,467 B2
(45) Date of Patent: Jul. 10, 2007

(54) METHOD AND APPARATUS FOR HIGH-RESOLUTION DEFECT LOCATION AND CLASSIFICATION

(75) Inventor: Joachim Wienecke, Jena (DE)

(73) Assignee: Vistec Semiconductor Systems Jena GmbH (DE)

( * ) Notice: Subject to any disclaimer, the term of this patent is extended or adjusted under 35 U.S.C. 154(b) by 404 days.

(21) Appl. No.: 10/840,730

(22) Filed: May 6, 2004

(65) Prior Publication Data
US 2004/0233422 A1 Nov. 25, 2004

(30) Foreign Application Priority Data
May 22, 2003 (DE) .................................. 103 23 139

(51) Int. Cl.
G01N 21/00 (2006.01)
G02B 27/40 (2006.01)
G06K 9/00 (2006.01)

(52) U.S. Cl. .............................. 356/237.5; 356/237.2; 250/201.3; 382/145

(58) Field of Classification Search .. 356/237.1–237.6; 250/559.42, 559.48, 201.3, 208.1; 382/149, 382/154, 159
See application file for complete search history.

(56) References Cited

U.S. PATENT DOCUMENTS

| | | | |
|---|---|---|---|
| 5,038,048 A * | 8/1991 | Maeda et al. .......... 250/559.41 |
| 5,108,176 A * | 4/1992 | Malin et al. ............. 356/243.1 |
| 5,153,444 A | 10/1992 | Maeda et al. | |
| 5,801,965 A * | 9/1998 | Takagi et al. .................. 702/35 |
| 5,859,698 A | 1/1999 | Chau et al. | |
| 5,982,920 A * | 11/1999 | Tobin et al. ................. 382/145 |
| 5,982,921 A | 11/1999 | Alumot et al. | |
| 6,256,093 B1 * | 7/2001 | Ravid et al. ............. 356/237.2 |
| 6,566,671 B1 * | 5/2003 | Yoshida et al. .......... 250/559.4 |
| 6,608,295 B2 * | 8/2003 | Engelhardt ............... 250/201.3 |
| 6,710,868 B2 * | 3/2004 | Guetta ...................... 356/237.1 |
| 6,765,201 B2 * | 7/2004 | Uto et al. .................... 250/307 |

FOREIGN PATENT DOCUMENTS

| | | |
|---|---|---|
| EP | 0 524 348 A1 | 1/1993 |
| WO | WO 99/14575 | 3/1999 |
| WO | WO 99/67626 | 12/1999 |
| WO | WO 00/02037 | 1/2000 |

* cited by examiner

Primary Examiner—Sang H. Nguyen
(74) Attorney, Agent, or Firm—Houston Eliseeva, LLP

(57) ABSTRACT

In the manufacture of integrated circuits on a wafer, it is necessary to monitor the manufacturing process by inspecting the ICs as to whether errors or defects have occurred during production. It is already known to use a scattered-light device (32) to determine whether a defect is present on the wafer. According to the present invention, defect examination is now improved in that defect-suspected regions (33) are identified using the scattered-light device (32). With a further examination system (30, 28) different from the scattered-light device (32), a determination is then made as to whether the defect-suspected regions (33) are defects. The latter can then also be classified.

11 Claims, 3 Drawing Sheets

METHOD AND APPARATUS FOR HIGH-RESOLUTION DEFECT LOCATION AND CLASSIFICATION

RELATED APPLICATIONS

This application claims priority of the German patent application 103 23 139.0 which is incorporated by reference herein.

FIELD OF THE INVENTION

The invention concerns a method for examination of an object, in particular for high-resolution defect location and classification. Furthermore, the invention concerns and an apparatus for examination of an object, in particular for high-resolution defect location and classification of defects of an object.

BACKGROUND OF THE INVENTION

The manufacture of integrated circuits (ICs) is concentrated not only on memory circuits but also on the production of application-specific integrated circuits (ASICs). A cost-effective and high-quality manufacturing method for ICs requires a consistently flexible and automatic wafer production procedure that can be reliably managed, in particular, with the aid of a process monitoring and process control or regulation system. Particular emphasis is placed here on so-called defect inspection, i.e. the inspection of ICs to determine whether defects have occurred in the individual circuits during production. For this inspection, a suitable method must be selected from a series of possible methods. In the context of computerized or automatic methods, high-performance automatic defect detection systems based on image-image or image-data comparisons are especially suitable.

One such method is known, for example, from U.S. Pat. No. 5,153,444. On a wafer on which a plurality of identical IC circuits are applied, a defect is detected by comparing images of the individual ICs with one another. This is done by firstly acquiring a grayscale image of an IC. This grayscale image is then compared with the grayscale image of an adjacent IC. If the comparison reveals a point at which no conformity exists, this is regarded as a defect. Defect classification, however, requires a further examination of the two ICs, which must be performed at a second workstation.

While these systems are very accurate, they have the disadvantage that throughput times for defect detection are very long, several hours often being required for each wafer. Exact positioning of the individual images of the ICs with respect to one another is furthermore an absolute prerequisite for the reliability of the method. The acquisition and operating costs of such systems are also very high.

Defect inspection can also, on the other hand, be accomplished visually using inspection microscopes. Here, however, operating personnel are exposed to considerable physical stress. The inspection is moreover very time-intensive and error-prone. Scattered-light device have therefore been in use for some time for wafer inspection.

EP 0 524 348 discloses a scattered-light device of this kind. What is exploited here is the fact that very dense and fine defect structures of the surface defects generate not only scattered light but also a certain proportion of diffracted light, since the defect structures act as gratings. A light cone created in this fashion does not possess a local homogeneous intensity distribution. The defect structure can thus be identified using an optical arrangement in which an astigmatic lens system is arranged between the light source and the objective. This system generates a cigar-shaped intermediate image that is imaged by the objective onto the surface. A dark-field stop assembly arranged in the beam path between the lens system and the objective allows a direction-dependent measurement of the intensity produced by the defect structure, so that the latter can be detected. This embodiment of a scattered-light examination system for the inspection of wafers is very productive, but has only poor local resolution. In addition, the identified defect is difficult to distinguish from the background.

The wafer can also be examined pixel by pixel. Here, as proposed in WO 00/02037, a beam is directed vertically onto the wafer surface. The scattered radiation produced thereby at the beam incidence point is sensed using radially arranged detectors, and evaluated for each irradiation point, i.e. pixel by pixel, as to whether characteristics are present that indicate a pixel having defects or a defect-free pixel. This type of surface examination is, however, very memory-intensive and requires a great deal of time.

WO 99/14575 therefore proposes a refined method for scattered-light examination of surfaces in order to detect defect structures. Here the object to be examined is illuminated with a beam that is incident vertically onto the object, and simultaneously with a beam that is directed onto the object with a raking incidence. The two beams are polarized perpendicularly to one another. The scattered radiation generated by the respective incident beam is sensed by a separate detector. Better defect selectivity is thereby obtained, and can be even further improved by the additional application of image-processing methods.

U.S. Pat. No. 5,859,698 likewise discloses a method that allows the detection of defects by scattered-light examination. An automatic image processing system, which compares the image of a sample with a reference image, is used here. The resulting difference image can optionally be further evaluated using additional electronic methods, including morphological transformations or definition of a threshold value. The purpose of these electronic evaluations is to ascertain whether the data obtained from the difference image actually originated from a macrodefect.

In addition to reliable and automatic detection of defects, the defects that are detected also need to be classified. A method and a system for automatic defect classification (ADC) are known for this purpose from WO 99/67626. Here a small region of a wafer is illuminated with a laser beam. Four equally distributed dark-field detectors are arranged in such a way that their sensing angles overlap, thereby forming so-called detection zones. The scattered radiation sensed by the dark-field detectors is converted into electrical signals and conveyed to an analysis unit. The analysis unit is capable of detecting, from the electrical signals, whether a defect is in fact present. Using stored pattern evaluation methods, the analysis unit can additionally perform a classification of the defect, for example according to its size.

U.S. Pat. No. 5,982,921 proposes an apparatus and a method for defect identification on wafer surfaces. In a first phase of the method, the entire surface of an object is optically examined at relatively high speed. Advantageously, a laser beam is used for this purpose to scan the object. The result is then compared with a reference pattern. If specific points suspected of being defects are identified, those points are then examined more closely at higher resolution in a second phase of the method, to determine whether a defect in fact exists. Two mutually independent examination devices are provided to allow the examination to be performed in the individual phases. After examination of the object at the first device, it is transported to the location of the second examination device.

SUMMARY OF THE INVENTION

It is the object of the present invention to propose an improved method for high-resolution defect location and classification.

The above object is achieved by a method which comprises the steps of:
providing a scattered-light device;
illuminating the object with light from the scattered-light device;
evaluating a scattered radiation proceeding from the object;
determining defect-suspected regions of the object with the use of the scattered-light device; and
examining the determined defect-suspected regions with a high-resolution optical system.

It is a further object of the present invention to propose an improved apparatus for high-resolution defect location and classification.

The above object is achieved by an apparatus comprising: a scattered-light device that illuminates the object and evaluates a scattered-light radiation proceeding from the object, and an examination device, in particular a high-resolution optical system, for examination of the object is furthermore provided selectably in the apparatus.

The invention thus makes available a method and an apparatus in which an object is first examined as to whether so called "defect-suspected" regions are present, i.e. regions that, upon examination, exhibit properties that indicate a defect or a region having defects. The examination is performed using a scattered-light device. The coordinates of the defect-suspected regions are preferably stored. If the entire surface of the object is first examined with the scattered-light device, it is thereby also possible to prepare a kind of map or so-called electronic image of the surface of the object, the positions of the defect-suspected regions being marked. The defect-suspected regions can be recorded in a so-called scatter defect list.

Subsequent thereto, the defect-suspected regions are examined using a suitable method different from scattered-light examination. This determines whether the defect-suspected regions identified in the first step are in fact defects. All methods in which defects can actually be identified are, per se, usable for this examination. In particular, optically magnifying methods with objectives, and subsequent comparison of the resulting image with a reference image, can be used here. Depending on the desired resolution or magnification, other magnifying examination methods such as AFM or SEM can also be used.

If the scattered-light device is used in an optical microscope in combination with optical objectives for subsequent magnifying examination of the object, it is particularly advantageous to provide the scattered-light device and the objectives on an objective turret. In this fashion, the object can first be examined for defect-suspected regions using the scattered-light device. Once this examination is complete, the desired objective can be brought into its examination position by rotating the turret. Since the positions of the defect-suspected regions are stored, for example, in the scatter-defect list, they can be examined more closely with the objective, for example at moderate magnification. It is thus possible to identify, from among the defect-suspected regions, those that actually have defects. It is thereby possible to draw up a defect list that encompasses only the positions of those regions that actually have a defect.

If a further objective permitting a higher magnification is provided in the objective turret, the defect list can be worked through. This is done by rotating the high-magnification objective into the examination position and classifying all the defects by closer examination using the high-magnification objective. An image-image comparison, an image-data comparison, or an image-rule comparison can be used to ascertain whether a defect is actually present, or to classify the defect. The images acquired with the objectives are compared, in this context, with a reference image or with reference data; or, as in the case of the image-rule comparison, the structural and defect-related properties of the object are used directly for defect determination.

The use according to the present invention of ordinary objectives and special sensors for scattered-light examination in an objective turret thus has the advantage that only one bench, and therefore only a reduced installation area, is needed for examination of the object. Enhanced safety for the wafer can furthermore be ensured, since the object needs to be handled only once for the examination. In addition, the defect-suspected regions and the defect regions can be rapidly located again, the results of the individual steps being well-correlated with one another. It is furthermore easily possible to implement an adaptive adjustment to the inspection task. Rapid sensing of the surface of the object, in particular of the wafer, using scattered-light sensors can precede a detailed inspection of selected defect-suspected regions at low to moderate resolution. Classification of the defects can then be performed with single-point high-resolution optics, up to the point of using an AFM.

BRIEF DESCRIPTION OF THE DRAWINGS

Further advantages and advantageous embodiments of the invention are the subject matter of the Figures below and their portions of the description. In the individual Figures.

DETAILED DESCRIPTION OF THE INVENTION

Figure 1:
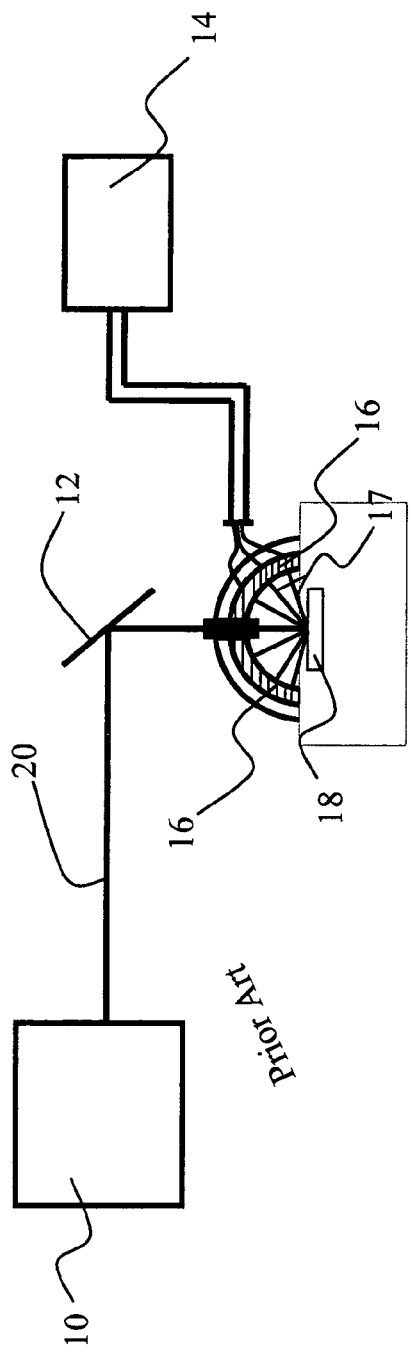
FIG. 1 shows a known defect examination apparatus.

FIG. 1 shows a scattered-light device for defect examination as known from the existing art. In a light source 10, for example a laser diode, a light beam 20 is generated and is directed via a mirror 12 onto an object 18, e.g. a wafer, to be examined. The scattered radiation 17 thereby produced is sensed by two sensor arms 16 and forwarded to a CCD camera 14. Evaluation of the scattered light using CCD camera 14 allows the identification of possible defect regions of the object at low magnification, i.e. with a relatively large spot size for light beam 20 incident onto object 18. Evaluation of this measurement often yields pseudo-defects, however, which must be eliminated. In addition, a classification of the defects cannot be accomplished in the context of this examination, since object 18 is not correctly depicted visually. A subsequent examination of the possible defect regions that have been identified is thus unavoidable.

Figure 2:
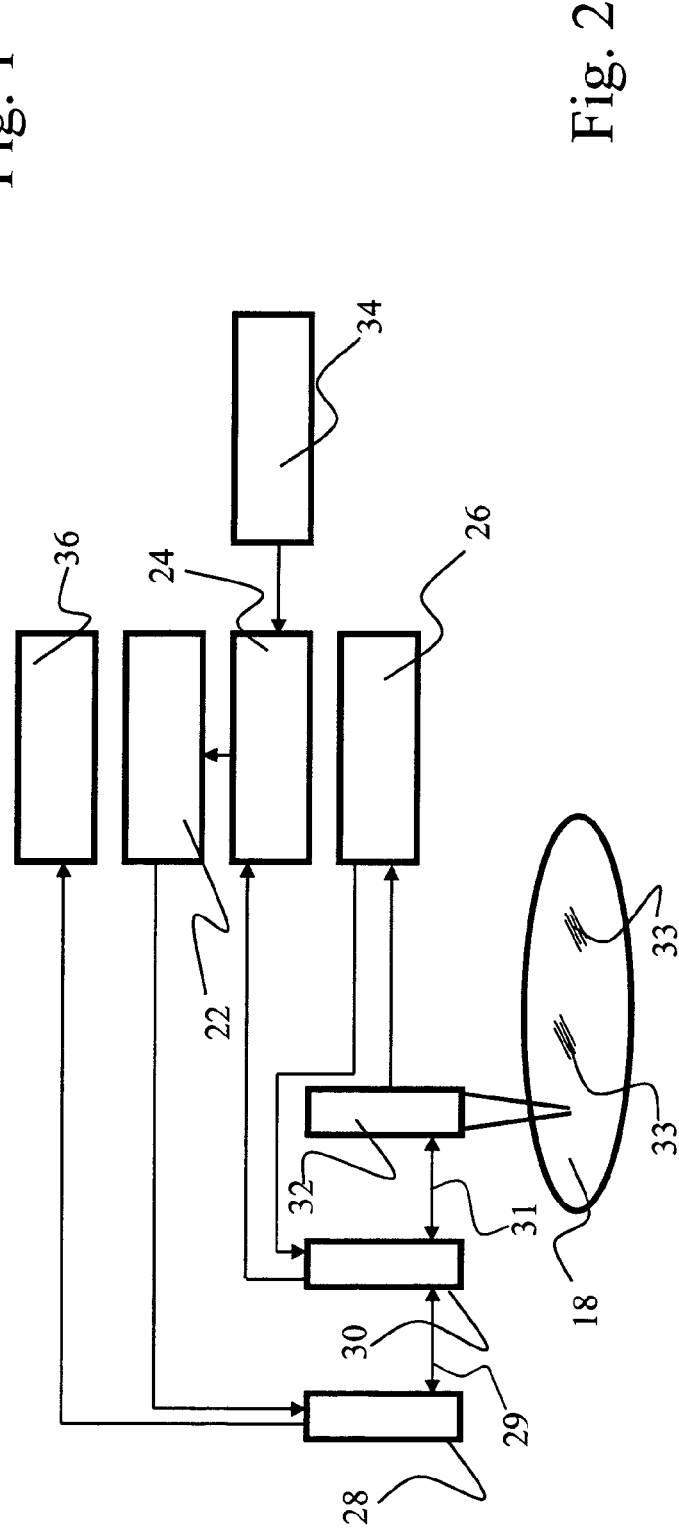
FIG. 2 shows the basic method sequence according to the present invention.

As depicted schematically in FIG. 2, according to the present invention the scattered-light examination is combined with the subsequent examination into one overall examination system. Here object 18 is first scanned with a scattered-light unit 32 using a relatively large spot size for the examining light beam. A scatter-defect list containing regions 33 possibly having defects is thereby obtained. A digital image of the surface of object 18 is thus prepared, which also contains the coordinates of the defect regions and is stored in a memory device 26.

In a step subsequent thereto, examination of the object is continued using the data obtained from the scattered-light examination. An optical examination device, for example an objective 30 of low resolution, is used for this purpose. The magnification selected for this purpose can be, for example, 5X for dark-field imaging using a laser as light source. The scattered-light device is moved out of the examination position and objective 30 is guided into the examination position, as indicated schematically by double arrow 31. Using objective 30 and the data obtained from the previous scattered-light examination, the possible defect regions 33 can then be examined as to whether defects are actually present. An image obtained using the objective can then be compared, for example in a comparison device 24, with a reference image that is stored in a reference image memory 34. From this comparison, a defect list can then be generated containing the data that are relevant to the actual defect regions. Those data can be stored in a defect memory 22.

The examination can then be continued in order to classify the defect, a high-resolution examination of the identified defect regions being accomplished. For this examination, objective 30 is removed from its examination position and high-resolution examination device 28 is brought into the examination position, as indicated by double arrow 29. The high-resolution examination can be performed, for example, with a high-resolution objective at 50× magnification and with confocal diffraction. The image values thereby obtained are conveyed to a defect classifier 36 with which the type of defect can be determined.

Figure 3:
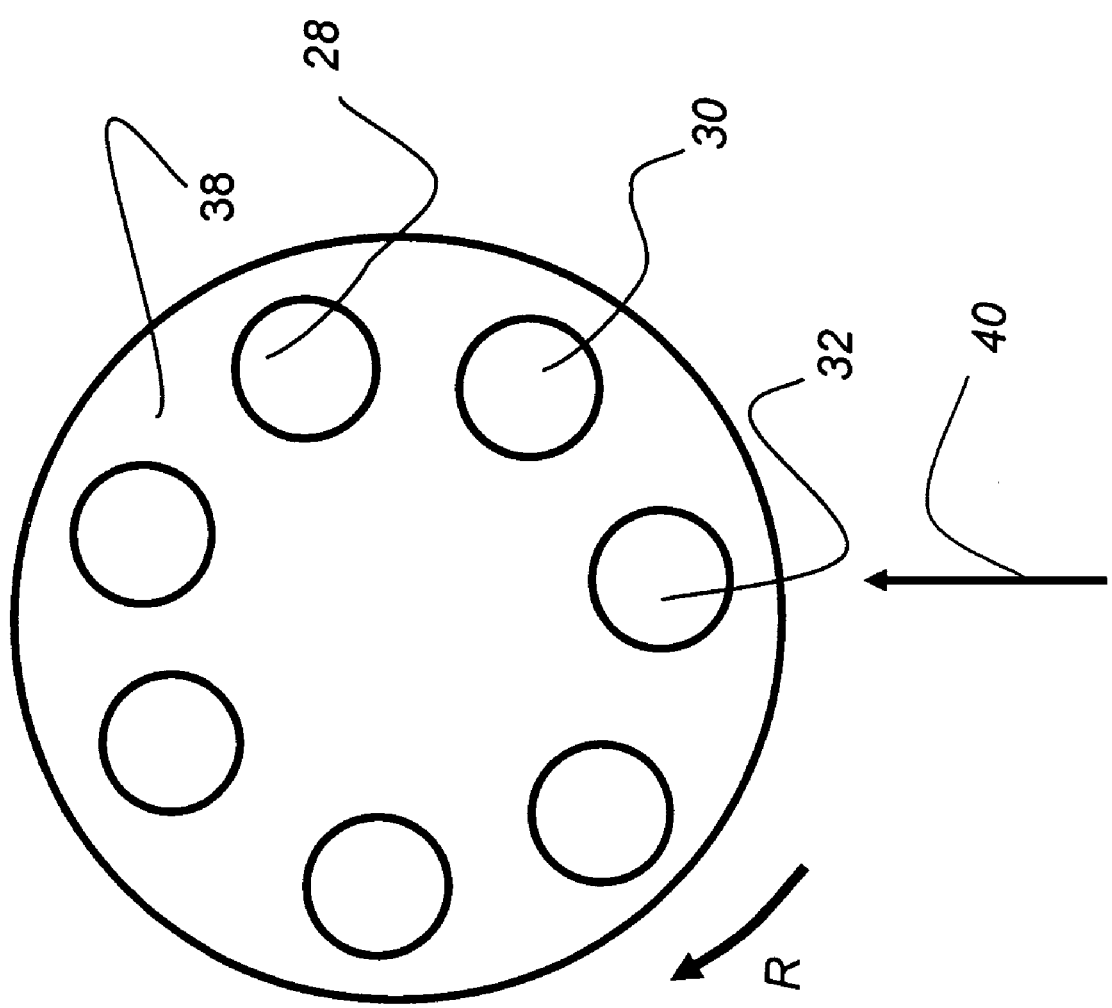
FIG. 3 shows examination devices mounted on an objective turret.

Scattered-light device 32, objective 30, and high-resolution examination device 28 can be accommodated, for example, in a microscope. As depicted in FIG. 3, it is particularly advantageous if each of these examination devices is provided at one position of an objective turret 38. Scattered-light device 32 can therefore first be rotated into the examination position. After completion of the scattered-light examination, objective 30 is rotated in rotation direction R into examination position 40, and the possible defect regions 33 are examined, in which context separate handling of object 18 can be dispensed with. After completion of the examination with object 18, high-resolution examination of the object 18 can be performed. For this, high-resolution examination device 28 is rotated in rotation direction R into examination position 40.

With the mounting of examination devices 28, 30, 32 on turret 38, it becomes much easier to return, for further examination, to the possible defect regions and the actual regions having defects. All that is used is the coordinate system of the microscope, thus excluding a priori problems related to equipment engineering or arising from different coordinate measuring system. It is furthermore possible to eliminate the complexity resulting from the use and handling of different items of equipment.

Figure 4:
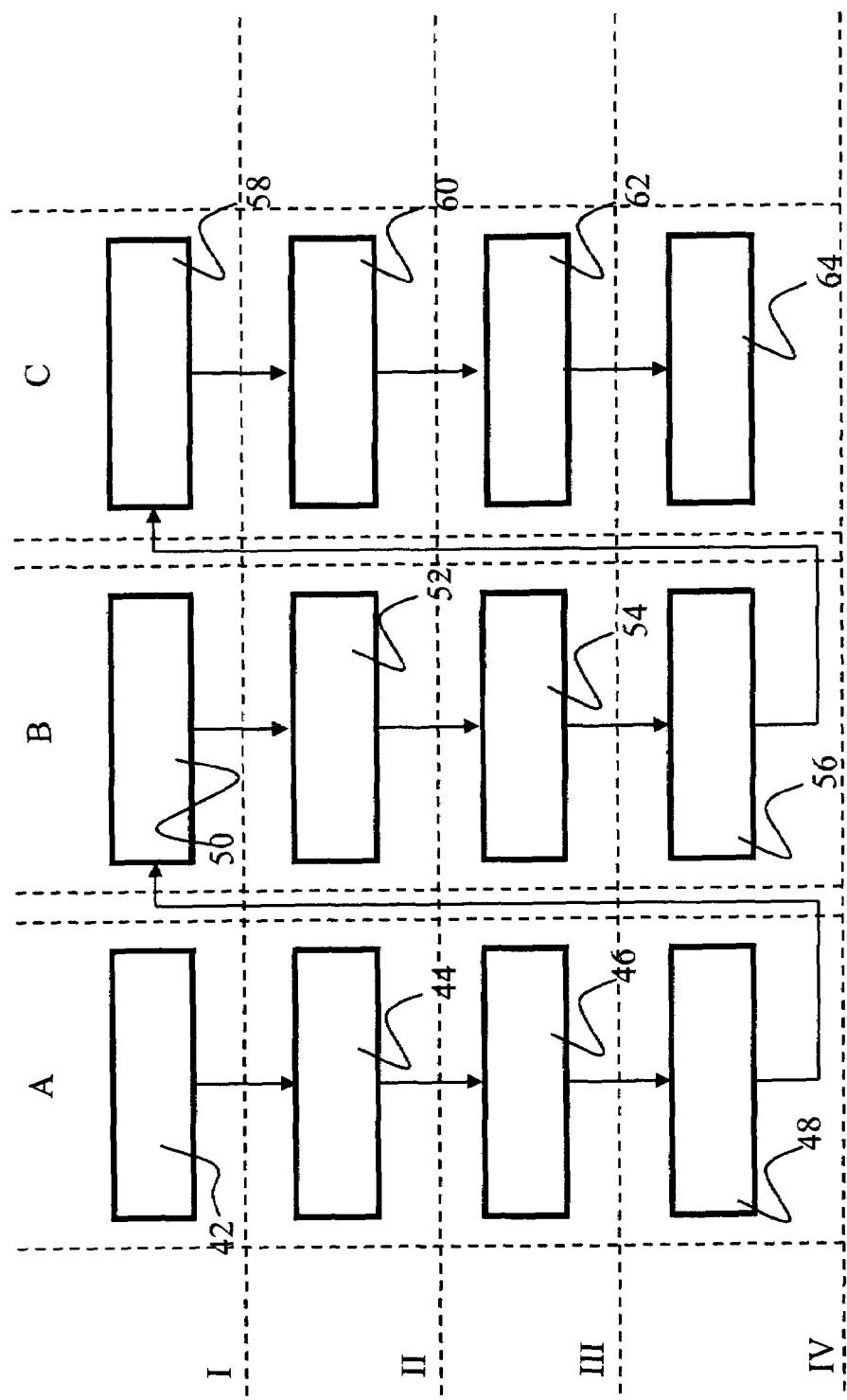
FIG. 4 shows, in detail, one possible method sequence corresponding to the invention.

The schematic overview of FIG. 4 shows the overall method according to the present invention in summary fashion. A division is made both into different classes I-IV and, concurrently therewith, into different resolution stages A, B, and C. The classes are depicted in rows, class I containing information that is already available. Class II encompasses the examination protocols used in each case, class III the inspection types, and class IV the results achieved. The stages proceed from stage A, which represents examination at low resolution to locate possible defect regions; through stage B in which the actual defect identification is performed; to stage C, in which the defects are classified and evaluated.

According to the present invention, the method begins in stage A with scattered-light examination of object 18, no information being present at the beginning 42 of the method. A complete inspection 44 of object 18 is performed, defect-suspected regions 33 being identified using optical methods 46 and recorded in a scatter-defect list 48.

In stage B, information is already available about defect-suspected regions 33 that are to be examined further, so that inspection regions 50 are known. For more detailed examination of inspection regions 50, a statistical control 52 is performed, preferably as image processing with real-time classification 54. This examination yields a defect list 56 that contains only those defects of object 18 that are actually present.

In stage C, measurement locations 58 for high-resolution measurement are known in accordance with defect list 56. A defect analysis 60 is performed, resulting—in the context of a detailed image analysis—in a defect classification 62 so that, for example, the identified defects can be divided into specific categories. The result of this is a weighted defect list 64.

The weighted defect list can be used to evaluate usable circuits on the wafer being examined, or also to improve the manufacturing process.

What is claimed is:

1. A method for examining an object for high-resolution defect location and classification of defects in the object, comprising the step of:

providing an apparatus comprising a scattered-light device and non scattered-light magnifying examination device;

illuminating the object with light from the scattered-light device and determining defect-suspected regions of the object by detecting a scattered radiation from the object;

examining the defect-suspected regions by a method different from scattered light examination by selectably using the non scattered-light magnifying examination device;

preparing an electronic image comprising defect-suspected regions of a surface the object by using data obtained from the scattered-light device; and recording positions of the defect-suspected regions in a scattered-defect list.

2. The method as defined in claim 1, further comprising selectably positioning the non scattered-light magnifying examination device in an examination position after positioning the scattered-light device in the examination position for examination of the object.

3. The method as defined in claim 1, wherein the scattered-light device and the non scattered-light magnifying examination device are mounted at different positions of a turret.

4. The method as defined in claim 1, further comprising utilizing the scatter-defect list for examining the defect-suspected regions with the non scattered-light magnifying examination device.

5. The method as defined in claim 4, further comprising using the results of examination with the non scattered-light magnifying examination device to prepare a defect list comprising positions of defect regions.

6. The method as defined in claim 5, further comprising examining the defect regions with the non scattered-light magnifying examination device comprising an optical or scanning device and preparing a weighted defect list.

7. The method as defined in claim 6, further comprising using an image-image comparison, an image-data comparison, or an image-rule comparison method to examine the scatter-defect regions or defect regions.

8. A system for examination of an object, comprising:
an apparatus comprising a scattered-light device and a non scattered-light magnifying examination device, the scattered light device for serving to illuminate the object, and the non-scattered-light magnifying examination device for serving to selectably examine the object, wherein the scattered-light device and non-scattered light magnifying examination device are selectably positionable in an examination position for examination of the object, wherein he scattered-light device and non-scattered light magnifying examination device are mounted on a turret, and wherein the scattered-light device is connected to a memory for storing positions of defect-suspected regions obtained with the scattered-light device.

9. The system as defined in claim 8, wherein the non-scattered light magnifying examination device comprises a microscope objective.

10. The system as defined in claim 8, wherein the non-scattered light magnifying examination device comprises an atomic force microscope.

11. A method for examining an object for high-resolution defect location and classification of defects in the object, comprising the steps of:
providing a scattered-light device and a high resolution objective mounted on a turret;
rotating the turret to place the scattered-light device into an examining position and illuminating the object with light from the scattered-light device;
determining defect-suspected regions of the object by detecting scattered radiation from the object; and
rotating the turret to place the high resolution objective into the examining position and examining the defect-suspected regions;
providing a low-to-moderate resolution objective on the turret; and
rotating the turret to place the low-to-moderate resolution objective into the examination position after determining detect-suspected regions of the object by detecting scattered radiation from the object.

* * * * *

UNITED STATES PATENT AND TRADEMARK OFFICE
CERTIFICATE OF CORRECTION

PATENT NO.       : 7,242,467 B2
APPLICATION NO.  : 10/840730
DATED            : July 10, 2007
INVENTOR(S)      : Joachim Wienecke Page 1 of 1

It is certified that error appears in the above-identified patent and that said Letters Patent is hereby corrected as shown below:

Title Page, item (73) Assignee: delete "Vistee" and insert --Vistec--

Signed and Sealed this

Thirteenth Day of November, 2007

JON W. DUDAS
*Director of the United States Patent and Trademark Office*